(12) United States Patent
Tiefensee et al.

(10) Patent No.: US 6,197,283 B1
(45) Date of Patent: Mar. 6, 2001

(54) USING WITHOUT EMULSIONS AS THICKENERS IN COSMETIC AND PHARMACEUTICAL FORMULATIONS

(75) Inventors: Kristin Tiefensee, Westheim; Volker Schehlmann, Römerberg; Martin Rübenacker, Altrip, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/542,855

(22) Filed: Apr. 4, 2000

Related U.S. Application Data

(62) Division of application No. 09/186,384, filed on Nov. 5, 1998, now Pat. No. 6,099,829.

(30) Foreign Application Priority Data

Nov. 10, 1997 (DE) .............................. 197 49 618

(51) Int. Cl.⁷ ............................ A61K 7/42; A61K 7/44; A61K 31/74; A61K 7/00
(52) U.S. Cl. ...................... 424/59; 424/60; 424/78.02; 424/78.03; 424/78.08; 424/400; 514/937; 514/938; 514/939; 514/943
(58) Field of Search ............................ 424/59, 60, 78.02, 424/78.03, 78.08, 400, 401; 514/937, 938, 939, 943

(56) References Cited

U.S. PATENT DOCUMENTS

| | | | |
|---|---|---|---|
| 4,925,884 | 5/1990 | Hübner et al. | 523/340 |
| 5,292,800 | 3/1994 | Moench et al. | 524/801 |

FOREIGN PATENT DOCUMENTS

| | | |
|---|---|---|
| 3522419 | 6/1985 | (DE) . |
| 4217673 | 12/1993 | (DE) . |
| 0126528 | 11/1984 | (EP) . |
| 0297184 | 1/1989 | (EP) . |
| 0383057 | 8/1990 | (EP) . |
| 0503853 | 9/1992 | (EP) . |
| 95/35089 | 12/1995 | (WO) . |

Primary Examiner—Shelley A. Dodson
(74) Attorney, Agent, or Firm—Keil & Weinkauf

(57) ABSTRACT

W/O emulsions comprising dispersed therein crosslinked, water-swellable polymers consisting of a) 35–100% by weight of ionic monomers, b) 0–65% by weight of nonionic monomers, c) 0.3–1 mol-%, based on a) and b), of at least one at least bifunctional monomer, where the oil phase consists of one or more fatty acid esters, are used as thickeners in cosmetic or pharmaceutical formulations.

17 Claims, No Drawings

USING WITHOUT EMULSIONS AS THICKENERS IN COSMETIC AND PHARMACEUTICAL FORMULATIONS

This is a Divisional Application of application Ser. No. 09/186,384, filed on Nov. 5, 1998, now U.S. Pat. No. 6,099,829.

The invention relates to the use of W/O emulsions comprising crosslinked, water-swellable polymers dispersed therein as thickeners in cosmetic or pharmaceutical formulations. It also relates to W/O emulsions and to cosmetic and pharmaceutical formulations.

When formulating cosmetic or pharmaceutical preparations such as skin creams, skin lotions, gels and other cosmetic beauty products, and pharmaceutical skin preparations as well, use is made of crosslinked acrylic acid polymer stabilizers that are known under the CTFA name Carbomer. These polymers are precipitation polymers and constitute free-flowing powders which are neutralized following their incorporation into water by stirring. This neutralization step is necessary to convert the acidic polymers into the carboxylates, which are ultimately responsible for the rise in viscosity and hence the stabilization of the formulation. Disadvantages of these pulverulent polymers are their dustiness and, associated therewith, their poor wettability, which prolongs the period required for homogenization. It is not possible to rule out small amounts of residual solvent from the preparation process.

A nondusting polymer is described in EP 383 057. That patent relates to crosslinked acrylic acid polymers which include nitrile-containing comonomers and are prepared in a water/paraffin emulsion; the water is removed by distillation as an azeotrope. The emulsions described are employed in the printing of textiles, and are unsuitable for use in cosmetic products.

DE 35 22 419 describes the inverse emulsion polymerization of acrylamide with acrylic acid in one process step. The pH is in the alkaline range and is therefore unfavorable for cosmetic purposes, especially for skin applications.

A process for preparing water-soluble or water-swellable polymers in a W/O emulsion is claimed by EP 126 528, which comprises olymerizing the water-soluble monomers in the presence of emulsifiers and with addition of a specific dispersing system consisting of alkanols. The polymers are not intended for cosmetic applications.

Crosslinked acrylic acid polymers in a W/O emulsion are described, furthermore, in EP 297 184 as water absorbents. The degree of crosslinking is not more than 0.5 mol-%; an inverting agent is present. The concentration of emulsifiers is at least 5% of the total dispersion. The polymerization is started by oil-soluble initiators. Examples of the oil component used are olive oil and eucalyptus oil—in other words, oils which are unsaturated, and hence unstable, or have a strong odor.

DE 42 17 673 A1 discloses electrolyte-thickenable surfactant combinations as a base for cosmetic formulations. The surfactants and electrolytes necessary here for the thickening effect are disadvantageous for certain applications.

WO 95/35089 describes compositions which can be applied topically and which comprise a thickener. The thickener is a W/O emulsion with a crosslinked polymer and a volatile oil, such as a silicone or an isoparaffin, as organic phase.

EP 503 853 discloses water-soluble thickeners for cosmetic formulations, comprising a very specific comonomer (AMPS).

It is an object of the present invention to provide polymers which do not have the disadvantages of the powder products and which do permit simple formulation of cosmetic or dermatological preparations: good efficacy, easy wettability, self-inverting, able to be used without an additional neutralizing step, and giving a pH of 6–7. The end product should have a smooth appearance and in the case of skincare products should "break" easily on the skin.

We have found that this object is achieved by the use of W/O emulsions comprising dispersed therein crosslinked, water-swellable polymers consisting of
a) 35–100% by weight of ionic monomers,
b) 0–65% by weight of nonionic monomers,
c) 0.3–1 mol-%, based on a) and b), of at least one at least bifunctional monomer,
where the oil phase consists of one or more fatty acid esters, as thickeners in cosmetic or pharmaceutical formulations.

It is preferred to use W/O emulsions whose oil phase consists of polyglycerol fatty acid esters, especially fatty acid esters of a polyglycerol mixture, comprising di- and triglycerol, with caprylic and/or capric acid.

The invention additionally provides W/O emulsions comprising dispersed therein crosslinked, water-swellable polymers consisting of
a) 35–100% by weight of ionic monomers,
b) 0–65% by weight of nonionic monomers,
c) 0.3–1 mol-%, based on a) and b), of at least one at least bifunctional monomer, and
where the oil phase consists of one or more polyglycerol fatty acid esters of a polyglycerol mixture comprising diglycerol and triglycerol with fatty acid mixtures comprising caprylic and/or capric acid.

The invention also provides cosmetic or pharmaceutical formulations comprising a W/O emulsion comprising dispersed therein crosslinked, water-swellable polymers consisting of
a) 35–100% by weight of ionic monomers,
b) 0–65% by weight of nonionic monomers,
c) 0.3–1 mol-%, based on a) and b), of at least one at least bifunctional monomer, and
where the oil phase consists of one or more polyglycerol fatty acid esters.

The preferred end use of the W/O emulsions is in cosmetic formulations for skin or hair.

The W/O polymer dispersion described in the present invention is prepared by inverse emulsion polymerization. In the first step, an aqueous monomer solution is emulsified in an oil phase with W/O emulsifiers typical of these systems. The polymerization is started by free-radical initiators. Since the polymers are intended to function as thickeners, they must be in chemically crosslinked form. The crosslinker is preferably added to the monomer solution.

As monomers it is preferred to employ unsaturated $C_3$–$C_5$ carboxylic acids, such as acrylic acid, methacrylic acid, maleic acid (anhydride), fumaric acid (anhydride), itaconic acid or mixtures thereof. They can be homopolymerized or copolymerized with nonionic monomers. Suitable such compounds are unsaturated compounds which can be dissolved with the ionic monomers in water; examples thereof are acrylamide, methacrylamide, vinylpyrrolidone, vinylimidazole, vinylcaprolactam and hydroxyalkyl esters of carboxylic acids, such as hydroxyethyl acrylate. The proportion of ionic monomers in the overall monomer mixture is from 35 to 100%, preferably from 50 to 100%. Particular preference is given to an acrylic acid content of >90%.

From 5 to 80%, preferably from 10 to 50%, of the ionic monomers are in neutralized form. Neutralization can in principle be carried out using all bases which satisfy cosmetic requirements. Use is made preferably of triethanolamine, NaOH and tetrahydroxypropylethylenediamine, for example. Mixtures of bases are also possible.

The concentration of the monomers in the aqueous solution prior to polymerization is from 10 to 60%.

The polymer is crosslinked by copolymerizing the monomers with at least diunsaturated water- or oil-soluble compounds. Suitable such compounds are methylenebisacrylamide, divinylpyrrolidone, allyl (meth)acrylate, triallylamine, ethylene glycol diacrylates (up to 50 EO), (meth)acrylic esters of dihydric or higher polyhydric alcohols, such as trimethylolpropane triacrylate or pentaerythritol tetraacrylate; the alcohol functions can in this case carry up to 50 EO groups and can each have different degrees of ethoxylation. These crosslinkers are present in amounts of from 0.3 to 1 mol-% individually or as a mixture. Water-soluble crosslinkers are preferred.

The oil phase consists of one or more fatty acid esters. These components of the invention have a positive effect on the cosmetic formulation (appearance, sensation on the skin). Examples of such components are fatty acid isopropyl esters, such as isopropyl palmitate or isopropyl myristate, or polyglycerides of fatty acids, especially fatty acid mixtures comprising at least 50% of caprylic and/or capric acid. Preference is given to polyglycerol fatty acid esters based on a polyglycerol mixture comprising essentially mono-, di-, tri- and tetraglycerol, especially di- and triglycerol. The proportion of the oil phase in the overall emulsion is 15–70%, preferably 20–35%.

The water phase is dispersed in the organic phase using W/O emulsifiers that are known for this purpose. The HLB [hydrophilic/lipophilic balance; cf. W. C. Giffin, J. Soc. Cosmet. Chem. 1, (1950) 311] of the emulsifiers used is from 4 to 8. Examples of such emulsifiers are sorbitan monooleate, sorbitan monostearate, glyceryl monostearate, block copolymers of hydroxy fatty acid polyesters and polyoxyethylene. They can be employed alone or in combination in overall concentrations of from 2 to 10%, preferably from 2 to 5% of the overall emulsions.

It is also possible to add emulsifiers having an HLB of more than 8 to the emulsion, in concentrations of from 0.25 to 7% of the overall emulsion. Examples of such emulsifiers are ethoxylated $C_6$–$C_{12}$-nonylphenols and $C_{12}$–$C_{18}$ fatty alcohols; the degree of ethoxylation is from 5 to 20 mol-%.

The emulsification of the aqueous phase in the oil phase does not necessitate any special equipment; instead, the aqueous monomer phase can be emulsified in a standard polymerization vessel by stirring with, for example, an anchor stirrer. The stirrer speed depends on the geometry of the reactor and is from 30 to 400 rpm.

Initiators which can be employed include water- and/or oil-soluble free-radical initiators, such as alkali metal or ammonium peroxodisulfates, hydrogen peroxide, organic peroxides, with or without redox partners, or azo initiators. It is also possible to employ initiators with different decomposition temperatures, together or in succession. Based on the monomer mixture, from 0.05 to 0.5% of initiator is used, preferably from 0.05 to 0.3%.

The temperature at which polymerization takes place is from 20 to 150° C.; it can be kept constant or altered discontinuously (in order, for example, to raise the conversion by increasing the temperature). The polymerization produces water-in-oil emulsions with a solids content of from 10 to 40%, preferably from 15 to 35%. The solids content can be increased by complete or partial dewatering of the emulsions by means of distillation.

The W/O emulsions of crosslinked polymers according to the invention are employed as thickeners in, preferably, cosmetic or pharmaceutical applications. The polymers are not isolated but are employed directly in the W/O emulsion form. Typical use concentrations are from 0.1 to 0.8%, preferably from 0.2 to 0.5%, of active substance (polymer). The thickening action of the W/O emulsion begins directly after it is mixed with the cosmetic O/W emulsion; in order to attain the optimum effect, it is not necessary to add an inverting agent. Even purely aqueous systems can be thickened, and a cream gel is obtained.

EXAMPLES

General Instructions for Preparing the Polymer Emulsions

A 2 l polymerization vessel equipped with anchor stirrer, thermometer, nitrogen inlet and nitrogen outlet is charged with each of the monomer emulsions indicated below. The polymerizable mixture is emulsified under a stream of nitrogen for 30 minutes with half the amount of the initiator. Polymerization is conducted subsequently by raising the temperature to 50–55° C. Following the addition of the second half of the initiator, the emulsion is postpolymerized at 55–65° C. for 2 h. Then it is cooled to room temperature.

Table 1 indicates the individual Examples 1–9 with the substances employed in each case. In Table 1, the indices denote the following substances:

1) Caprylic/capric triglycerides (Hüls AG, comprising 50–65% caprylic and 30–45% capric acid)
2) Sorbitan monooleate (ICI)
3) ABA block copolymers of a hydroxystearic acid condensate and polyethylene glycol (ICI)
4) 2,2'-Azobis(2-amidinopropane)dihydrochloride (Wako), T (t=10 h)=56° C. 2,2'-Azobis(N,N'-dimethyleneisobutyramidine)dihydrochloride (Wako), T (t=10 h)=44° C.

All batches contain 0.02% of the pentasodium salt of diethylenetriaminepentaacetic acid.

TABLE 1

| Starting materials | Ex. 1 Emulsion A | Ex. 2 Emulsion B | Ex. 3 Emulsion C | Ex. 4 Emulsion D | Ex. 5 Emulsion E | Ex. 6 Emulsion F | Ex. 7 Emulsion G | Ex. 8 Emulsion H | Ex. 9 Emulsion I |
|---|---|---|---|---|---|---|---|---|---|
| Water | 520 g | 500 g | 500 g | 310 g | 280 g | 440 g | 500 g | 440 g | 440 g |
| Acrylic acid | 218 g | 218 g | 218 g | 218 g | 218 g | 150 g | 218 g | 218 g | 218 g |
| NaOH 40% strength | — | 150 g | 150 g | 227 g | 227 g | 21 g | 150 g | 150 g | 150 g |
| Triallylamine | | | 2.5 g | | | | | | |

TABLE 1-continued

| Triethanol-amine | 89.6 g | | | | | | | | — |
|---|---|---|---|---|---|---|---|---|---|
| Acryl-amide 50% strength | — | — | — | — | — | 145 g | — | | |
| Divinyl-pyrrolidone | 2.5 g | 2.5 g | | 2.5 g | 2.5 g | 2.5 g | 2.5 g | 2.5 g | 2.5 g |
| Miglyol 812[1)] | 275 g | 275 g | 275 g | 275 g | 275 g | 275 g | 275 g | 275 g | 275 g |
| Span 80[2)] | 16.5 g (1.5%) | 16.5 g | 16.5 g | 16.5 g | 33 g | 16.5 g | 16.5 g (1.5 g) | 11.0 g | 11.0 g |
| Arlacel P 135[3)] | 5.5 g (0.5%) | 5.5 g | 5.5 g | 5.5 g | 11 g | 5.5 g | 5.5 g (0.5%) | 11.0 g | 11.0 g |
| Stearyl alcohol + 20 mol of EO | | | | | | | — | — | 5.5 g |
| Wako V 50[4)] 6% strength | 2 × 0.8 g | 2 × 0.8 g | 2 × 0.8 g | 2 × 0.8 g | 2 × 0.8 g | 2 × 0.8 g | 0.8 g | 2 × 0.8 g | 2 × 0.8 g |
| Wako V 44[5)] | | | | | | | 0.8 g | | |

| | Comparative examples | |
|---|---|---|
| Starting material | Emulsion 1 | Emulsion 2 |
| Water | 280 g | 280 g |
| Acrylic acid | 218 g | 218 g |
| NaOH 40% strength | 227 g | 227 g |
| Divinylpyrrolidone | 2.5 g | 2.5 g |
| Liquid paraffin | 275 g | |
| Abil 100[4)] | | 275 g |
| Sorbitan monooleate[1)] | 11.0 g | 11.0 g |
| Arlacel P 135[2)] | 11.0 g | 11.0 g |
| Wako V 50[3)] 6% strength | 2 × 0.8 g | 2 × 0.8 g |

[1)]Sorbitan monooleate (ICI)
[2)]ABA block copolymers of a hydroxystearic acid condensate and polyethylene glycol (ICI)
[3)]2,2'-Azobis(2-amidinopropane) dihydrochloride (Wako), T (t = 10 h) = 56° C.
[4)]Dimethylpolysiloxane Testing The W/O Emulsions The emulsions were employed in the formulations below. Parameters assessed were the viscosity (Brookfield RVT) and the appearance of the formulation. Said appearance was assessed on the basis of the coating of the formulation and was evaluated using the school-grade system from 1 to 5. "Texture" indicates lustre and surface quality, while "specks" identify small gel structures.

These are, inter alia, a measure of the invertability of the W/O emulsion. Texture: grade 1 denotes smooth surface, lustrous; grade 5 denotes a grainy surface, matt. Specks: grade 1 denotes structures visible, grade 5 means that there are clearly gel particles present.

| Gel with essential oils | | |
|---|---|---|
| 1% | Active substance (thickener) | |
| 49% | Water | |
| 10% | Ethanol | |
| 7.5% | Rosemary oil | |
| 7.5% | Pine needle oil | |
| 2% | Cremophor RH 40 | BASF, PEG 40 hydrog. castor oil |
| 0.1% | Euxyl K 100 | Schülke & Mayr, benzyl alcohol, methylchloroisothiazolinone |

Following the solubilization of the oil components, water and the thickener emulsion are added and the mixture is homogenized for 1 to 2 minutes.

| Body lotion | | | |
|---|---|---|---|
| A | 2% | Cremophor A6 | BASF, Ceteareth-6 (and) stearyl alcohol |
| | 2% | Cremaphor A 25 | BASF, Ceteareth-25 |
| | 6% | Almond oil | |
| | 3% | Imwitor 960 K | Hüls, glyceryl stearate SE |
| | 1.5% | Lanette 0 | Henkel, cetearyl alcohol |
| | 0.5% | Abil 100 | Wacker, dimethicone |
| | 8% | Luvitol EHO | BASF, cetearyl octanoate |
| B | 3% | 1,2-propylene glycol | |
| | 2% | Glycerol | |
| | 3% | Aloe vera gel | |
| | 0.3% | ACTIVE SUBSTANCE | |
| | 65.3% | Water | |
| C | 3% | Collagen CLR | |

Phases A and B are heated separately to 80° C. Phase B is homogenized in phase A. At 40° C., phase C is added and the mixture is homogenized.

| Sunscreen emulsion | | | |
|---|---|---|---|
| A | 0.25% | Pemulen TR 1 | B.F. Goodrich, acrylates/$C_{10}$—$C_{30}$-alkyl acrylate crosspolymer |
| | 7% | Uvinul MC 80 | BASF, octyl methoxycinnamate |
| | 3% | Octyl salicylate | |
| | 6% | Witconol APM | Witco, PPG-3 myristyl ether |
| | 1% | Uvinul M 40 | BASF, benzophenone-3 |
| | 0.2% | ACTIVE SUBSTANCE | |

-continued

Sunscreen emulsion

|   | 2%    | Luvitol EHO        | BASF, cetearyl octanoate      |
|---|-------|--------------------|-------------------------------|
|   | 0.2%  | (−)-α-bisabolol    |                               |
| B | 0.1%  | Natrosol 250 HR    | Aqualon, hydroxyethylcellulose |
|   | 0.05% | EDTA BD            | BASF disodium EDTA            |
|   | 3%    | 1,2-Propylene glycol |                             |
|   | 74.8% | Water              |                               |
| C | 0.2%  | Triethanolamine    |                               |

| Testing/emulsion | Ex. 1 A[1] | Ex. 2 B | Ex. 3 C | Ex. 4 D | Ex. 5 E | Ex. 6 F | Ex. 7 G | Ex. 8 H | Ex. 9 I | Comp. 1 | Comp. 2 |
|---|---|---|---|---|---|---|---|---|---|---|---|
| Gel with essential oils | | | | | | | | | | | |
| Viscosity | 57 | 148 | 115 | 84 | 70 | 60 | 142 | 102 | 123 | 47 | 69 |
| Texture | 1.5 | 1.0 | 1.5 | 1.5 | 1.5 | 2 | 1.5 | 2 | 2 | 3.5 | 4 |
| Specks | 1.5 | 1.5 | 1.5 | 1.5 | 2 | 1.5 | 1.5 | 2 | 1.5 | 4 | 4 |
| Body lotion | | | | | | | | | | | |
| Viscosity | 9 | 26 | 23 | 18 | 21 | 20 | 25 | 18 | 21 | 7 | 9 |
| Texture | 1.5 | 1.5 | 1.0 | 1.5 | 1.5 | 1.5 | 1.5 | 2 | 1.5 | 4 | 3.5 |
| Specks | 2.0 | 1.5 | 1.5 | 1.5 | 1.5 | 1.0 | 1.5 | 1.5 | 1.5 | 4 | 3.5 |
| Sunscreen emulsion | | | | | | | | | | | |
| Viscosity | 7 | 24 | 21 | 21 | 17 | 15 | 23 | 16 | 19 | 11 | 12 |
| Texture | 1.5 | 1.5 | 1.0 | 1.5 | 1.5 | 1.5 | 1.0 | 1.5 | 1.5 | 4 | 4 |
| Specks | 1.5 | 1.5 | 1.5 | 1.5 | 1.5 | 1.5 | 1.5 | 2.0 | 1.5 | 4.5 | 3.5 |

[1] Formulations that were thickened with emulsion A additionally comprise 0.2 g of triethanolamine as base

We claim:

1. A cosmetic or pharmaceutical preparation comprising an effective amount of a W/O emulsion, said W/O emulsion comprising dispersed therein crosslinked, water-swellable polymers consisting of
   a) 35–100% by weight of ionic monomers,
   b) 0–65% by weight of non-ionic monomers,
   c) 0.3–1 mol-%, based on a) and b), of one or more at least bifunctional monomer,
where the oil phase consists of one or more fatty acid esters, as a thickener, which cosmetic or pharmaceutical preparation is adapted as a sunscreen preparation for the treatment of skin.

2. The preparation defined in claim 1, wherein from 5 to 80% of the the ionic monomers are in neutralized form.

3. The preparation defined in claim 1, wherein the ionic monomer is a $C_3$–$C_5$ carboxylic acid.

4. The preparation defined in claim 1, wherein the ionic monomer is acrylic acid.

5. The preparation defined in claim 1, further comprising of from 0.25 to 7% by weight of an emulsifier.

6. The preparation defined in claim 5, which comprises of from 0.5 to 5% by weight of the emulsifier.

7. The preparation defined in claim 1, wherein the fatty acid esters comprise polyglycerides having a fatty acid component comprising capric acid, caprylic acid or a mixture of capric acid and caprylic acid.

8. The preparation defined in claim 7, wherein the fatty acid component comprises at least 50% of capric acid, caprylic acid or of a mixture of capric acid and caprylic acid.

9. The preparation defined in claim 1, wherein the fatty acid esters comprise triglycerides having a fatty acid component comprising capric acid, caprylic acid or a mixture of capric acid and caprylic acid.

10. The preparation defined in claim 1, wherein the fatty acid esters comprise
    i) of from 50 to 65% of caprylic acid, and
    ii) of from 30 to 45% of capric acid.

11. The preparation defined in claim 1, wherein the oil phase consists of fatty acid esters having a fatty acid component and an alcohol component, the alcohol component of said esters comprising di- or triglycerol or a mixture thereof.

12. The preparation defined in claim 11, wherein the alcohol component further comprises monoglycerol or tetraglycerol or a mixture thereof.

13. The preparation defined in claim 11, wherein the fatty acid component of the fatty acid esters comprise capric acid or caprylic acid or a mixture thereof.

14. The preparation defined in claim 12, wherein the fatty acid component of the fatty acid esters comprise capric acid or caprylic acid or a mixture thereof.

15. The preparation defined in claim 1, wherein the oil phase consists of fatty acid esters having a fatty acid component and an alcohol component, the fatty acid component of said fatty acid esters comprising at least 50% of capric acid or caprylic acid or a mixture of capric acid and caprylic acid.

16. The preparation defined in claim 15, wherein the fatty acid esters comprise triglycerides with or caprylic acid or capric acid or a mixture of capric acid and caprylic acid.

17. The preparation defined in claim 15, wherein the fatty acid component comprises
    i) of from to 65% of caprylic acid, and
    ii) of from 30% to 45% of capric acid.

* * * * *

UNITED STATES PATENT AND TRADEMARK OFFICE
CERTIFICATE OF CORRECTION

PATENT NO. : 6,197,283 B1
DATED : March 6, 2001
INVENTOR(S) : Tiefensee et al.

It is certified that error appears in the above-identified patent and that said Letters Patent is hereby corrected as shown below:

Item [54], the title should read:

-- USING W/O EMULSIONS AS THICKENERS IN COSMETIC AND PHARMACEUTICAL FORMULATIONS --.

ABSTRACT,
Item [57], delete the last three lines and substitute :

-- the oil phase of the W/O emulsion consists of polyglycerol fatty acid esters and comprises at least one fatty acid ester of diglycerol or triglycerol with with caprylic or capric acid, the W/O emulsions are useful as thickeners for cosmetic or pharmaceutical sunscreen compositions for the treatment of skin. --.

Column 8, claim 17,
Line 59, "from to 65%" should be -- from 50 to 65% --.
Line 60, "30% to 45% should be -- 30 to 45% --.

Signed and Sealed this

Twentieth Day of November, 2001

*Attest:*

NICHOLAS P. GODICI
*Attesting Officer*     Acting Director of the United States Patent and Trademark Office